United States Patent
Al-Herz et al.

(10) Patent No.: US 10,087,238 B2
(45) Date of Patent: Oct. 2, 2018

(54) METHOD OF PREVENTING MYOCARDIAL REPERFUSION INJURY IN REPERFUSION THERAPY BY ADMINISTERING INTRAVENOUS IMMUNOGLOBULIN

(71) Applicant: KUWAIT UNIVERSITY, Safat (KW)

(72) Inventors: Waleed Ebrahim Al-Herz, Kuwait (KW); Fawzi Abdalla Babiker, Safat (KW)

(73) Assignee: KUWAIT UNIVERSITY, Safat (KW)

( * ) Notice: Subject to any disclaimer, the term of this patent is extended or adjusted under 35 U.S.C. 154(b) by 0 days.

(21) Appl. No.: 15/439,807

(22) Filed: Feb. 22, 2017

(65) Prior Publication Data

US 2018/0237500 A1    Aug. 23, 2018

(51) Int. Cl.
| | |
|---|---|
| *A61P 9/10* | (2006.01) |
| *A61K 39/395* | (2006.01) |
| *C07K 16/00* | (2006.01) |
| *A61K 9/00* | (2006.01) |
| *C07K 16/18* | (2006.01) |

(52) U.S. Cl.
CPC ............ *C07K 16/00* (2013.01); *A61K 9/0019* (2013.01); *A61K 39/395* (2013.01); *A61P 9/10* (2018.01); *C07K 16/18* (2013.01)

(58) Field of Classification Search
None
See application file for complete search history.

(56) References Cited

U.S. PATENT DOCUMENTS

| | | |
|---|---|---|
| 2003/0170241 A1 | 9/2003 | Aukrust et al. |
| 2013/0273052 A1 | 10/2013 | Gies et al. |

FOREIGN PATENT DOCUMENTS

| | | |
|---|---|---|
| WO | WO 01/66124 A2 | 9/2001 |

OTHER PUBLICATIONS

Ueno et al (2007. Circulation. 116:II_99).*
Ueno, "Effect of intravenous administration of polyclonal immunoglobulin G on myocardial ischemia reperfusion injury", Fiscal 2009 results report, available at https://kaken.nii.ac.jp/report/KAKENHI-PROJECT-20790547/207905472009jisseki/, 1 page as printed; English translation attached.*
Araszkiewicz et al, 2013. Postep Kardiol Inter, 9, 3(33): 275-281.*

* cited by examiner

*Primary Examiner* — Zachary C Howard
(74) *Attorney, Agent, or Firm* — Richard C. Litman

(57) ABSTRACT

The method of preventing reperfusion injury in reperfusion therapy is a medical technique for prevention of reperfusion injury in a patient where reperfusion therapy is necessary, such as following myocardial infarction (MI) or heat transplant in the patient. The patient is treated with intravenous immunoglobulin (IVIG) prior to an ischemic event or, alternatively, following the ischemic event, with the intravenous immunoglobulin providing cardio-protective effects to the patient for preventing reperfusion injury. The treatment with the IVIG may be used with any suitable type of reperfusion therapy, such as thrombolytic therapy, coronary angioplasty or coronary artery bypass surgery.

5 Claims, 4 Drawing Sheets

METHOD OF PREVENTING MYOCARDIAL REPERFUSION INJURY IN REPERFUSION THERAPY BY ADMINISTERING INTRAVENOUS IMMUNOGLOBULIN

BACKGROUND OF THE INVENTION

1. Field of the Invention

The present invention relates to ischemia reperfusion therapy in a patient, and particularly to a method of preventing reperfusion injury by treatment with intravenous immunoglobulin (IVIG).

2. Description of the Related Art

Myocardial ischemia is a definite result of the reduction of blood flow and inadequate oxygen supply. Ischemia can induce various clinical conditions ranging from inflammation to myocardial damage and organ failure. Reperfusion is the traditional method for cardiac protection from ischemia. Reperfusion therapy is a medical treatment to restore blood flow, either through or around, blocked arteries. Thrombolytic therapy, coronary angioplasty, and coronary artery bypass surgery are examples of known reperfusion techniques. However, reperfusion itself can amplify or accelerate cell death, producing reperfusion-induced injury. Heart transplant patients are also susceptible to reperfusion injury due to the particular type of reperfusion performed with transplanted hearts.

Reperfusion of ischemic tissues is often associated with microvascular injury, particularly due to increased permeability of capillaries and arterioles that lead to an increase of diffusion and fluid filtration across the tissues. Activated endothelial cells produce more reactive oxygen species but less nitric oxide following reperfusion, and the imbalance results in a subsequent inflammatory response. The inflammatory response is partially responsible for the damage of reperfusion injury. White blood cells, carried to the area by the newly returning blood, release a host of inflammatory factors such as interleukins as well as free radicals in response to tissue damage. The restored blood flow reintroduces oxygen within cells that damages cellular proteins, DNA, and the plasma membrane. Damage to the cell's membrane may in turn cause the release of more free radicals. Such reactive species may also act indirectly in redox signaling to turn on apoptosis. White blood cells may also bind to the endothelium of small capillaries, obstructing them and leading to more ischemia.

With regard to therapies for treating reperfusion injury, therapeutic hypothermia is one of the most prevalent. In addition to therapeutic hypothermia, which involves the usage of highly specialized equipment, a variety of new drugs and compounds are being tested for treatment of reperfusion injury, including hydrogen sulfide treatment, cyclosporine, TRO40303, stem cell therapy, superoxide dismutase, and metformin. Each of these, however, is still under investigation, and each are uncommon treatments which may involve difficulty in obtaining the necessary materials, as well as incurring large costs. Thus, a method of preventing reperfusion injury in reperfusion therapy solving the aforementioned problems is desired.

SUMMARY OF THE INVENTION

The method of preventing reperfusion injury in reperfusion therapy is a medical technique for prevention of reperfusion injury in a patient where reperfusion therapy is necessary, such as following myocardial infarction (MI) or heat transplant in the patient. The patient is treated with intravenous immunoglobulin (IVIG) prior to an ischemic insult (IVIG pre-treatment) or, alternatively, following the ischemic insult (IVIG post-treatment), with the IVIG providing cardio-protective effects to the patient for preventing reperfusion injury. The treatment with the IVIG may be used with any suitable type of reperfusion therapy, such as thrombolytic therapy, coronary angioplasty or coronary artery bypass surgery, for example.

In either pre- or post-treatment of the patient with the intravenous immunoglobulin, the patient is given from about 0.5 g to about 2.0 g of the intravenous immunoglobulin per kilogram of patient body weight. This dosage may be a one-time dosage or may be delivered multiple times, dependent upon the particular situation.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1A:
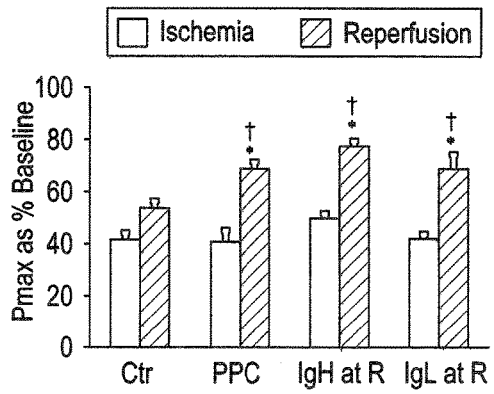
FIG. 1A is a graph comparing maximum developed pressure (Pmax) of the left ventricle function of a control sample group against a pacing post-conditioning (PPC) group, a group treated with the method of preventing reperfusion injury in reperfusion therapy with a high dose (1.0 g/kg) of immunoglobulin treatment (IgH) post-ischemia, and a group treated with the method of preventing reperfusion injury in reperfusion therapy with a low dose (0.6 g/kg) of immunoglobulin treatment (IgH) post-ischemic.
Figure 1B:
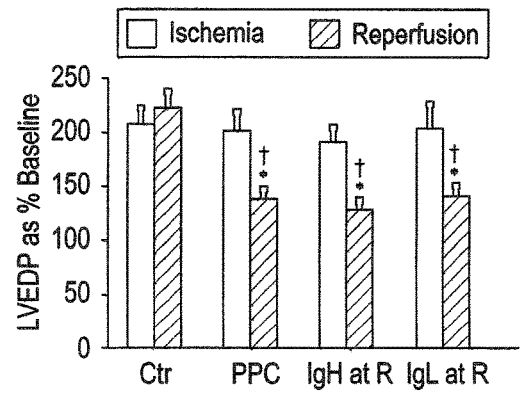
FIG. 1B is a graph comparing left ventricular end diastolic pressure (LVEDP) of the left ventricle function of a control sample group against a pacing post-conditioning (PPC) group, a group treated with the method of preventing reperfusion injury in reperfusion therapy with a high dose (1.0 g/kg) of immunoglobulin treatment (IgH) post-ischemia, and a group treated with the method of preventing reperfusion injury in reperfusion therapy with a low dose (0.6 g/kg) of immunoglobulin treatment (IgH) post-ischemia.
Figure 1C:
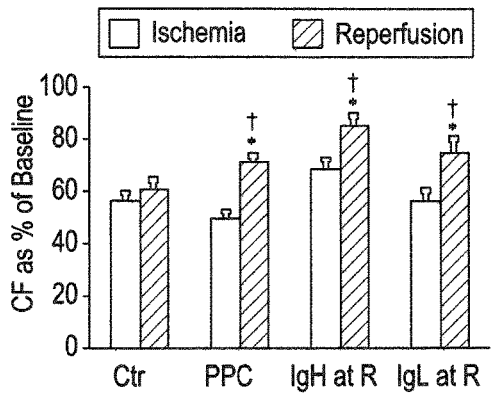
FIG. 1C is a graph comparing coronary flow (CF) of the coronary-vascular-dynamics of a control sample group against a pacing post-conditioning (PPC) group, a group treated with the method of preventing reperfusion injury in reperfusion therapy with a high dose (1.0 g/kg) of immunoglobulin treatment (IgH) post-ischemia, and a group treated with the method of preventing reperfusion injury in reperfusion therapy with a low dose (0.6 g/kg) of immunoglobulin treatment (IgH) post-ischemia.
Figure 1D:
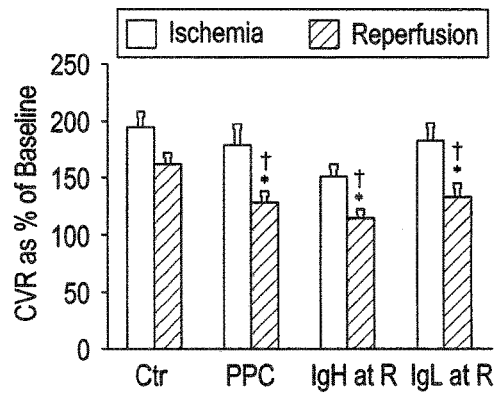
FIG. 1D is a graph comparing coronary vascular resistance (CVR) of the coronary-vascular-dynamics of a control sample group against a pacing post-conditioning (PPC) group, a group treated with the method of preventing reperfusion injury in reperfusion therapy with a high dose (1.0 g/kg) of immunoglobulin treatment (IgH) post-ischemia, and a group treated with the method of preventing reperfusion injury in reperfusion therapy with a low dose (0.6 g/kg) of immunoglobulin treatment (IgH) post-ischemia.
Figure 1E:
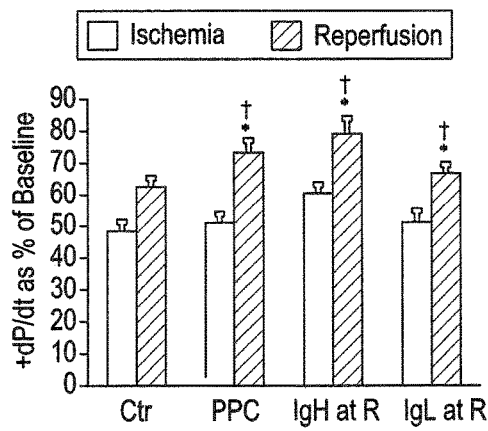
FIG. 1E is a graph comparing left ventricle (LV) contractility (+dP/dt) of a control sample group against a pacing post-conditioning (PPC) group, a group treated with the method of preventing reperfusion injury in reperfusion therapy with a high dose (1.0 g/kg) of immunoglobulin treatment (IgH) post-ischemia, and a group treated with the method of preventing reperfusion injury in reperfusion therapy with a low dose (0.6 g/kg) of immunoglobulin treatment (IgH) post-ischemia.
Figure 1F:
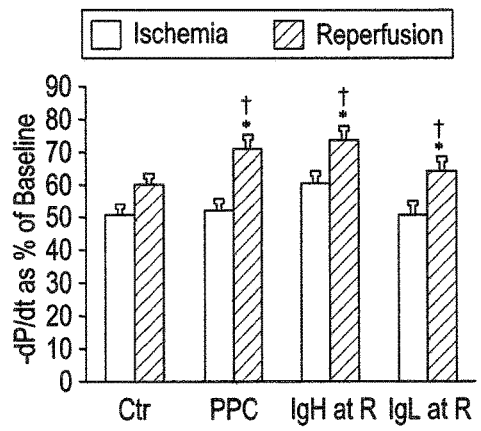
FIG. 1F is a graph comparing LV contractility (−dP/dt) of a control sample group against a pacing post-conditioning (PPC) group, a group treated with the method of preventing reperfusion injury in reperfusion therapy with a high dose (1.0 g/kg) of immunoglobulin treatment (IgH) post-ischemia, and a group treated with the method of preventing reperfusion injury in reperfusion therapy with a low dose (0.6 g/kg) of immunoglobulin treatment (IgH) post-ischemia.
Figure 2A:
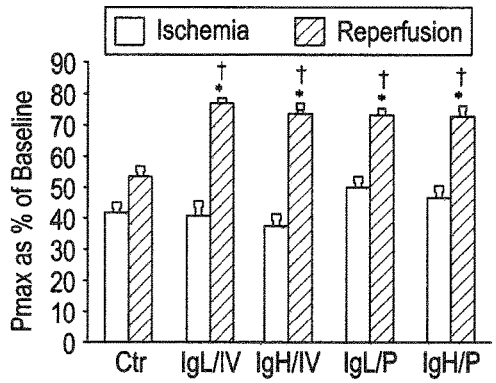
FIG. 2A is a graph comparing maximum developed pressure (Pmax) of the left ventricle function of a control sample group against a pacing post-conditioning (PPC) group, a group treated with the method of preventing reperfusion injury in reperfusion therapy with a high dose (1.0 g/kg) of immunoglobulin treatment (IgH) pre-ischemia, and a group treated with the method of preventing reperfusion injury in reperfusion therapy with a low dose (0.6 g/kg) of immunoglobulin treatment (IgH) pre-ischemia.
Figure 2B:
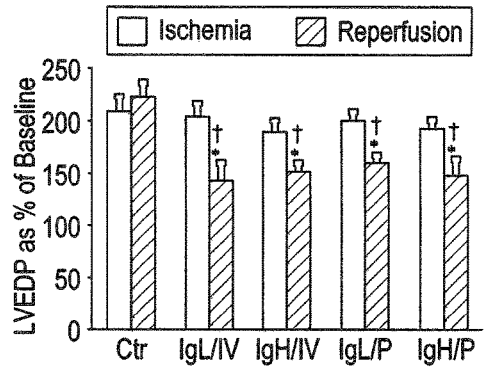
FIG. 2B is a graph comparing left ventricular end diastolic pressure (LVEDP) of the left ventricle function of a control sample group against a pacing post-conditioning (PPC) group, a group treated with the method of preventing reperfusion injury in reperfusion therapy with a high dose (1.0 g/kg) of immunoglobulin treatment (IgH) pre-ischemia, and a group treated with the method of preventing reperfusion injury in reperfusion therapy with a low dose (0.6 g/kg) of immunoglobulin treatment (IgH) pre-ischemia.
Figure 2C:
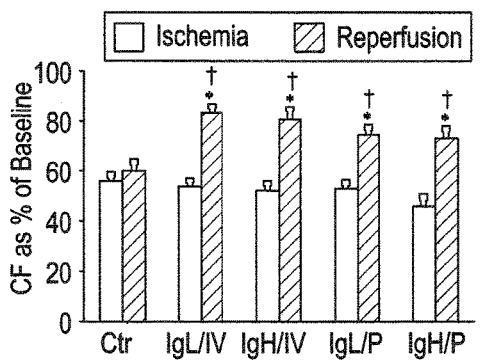
FIG. 2C is a graph comparing coronary flow (CF) of the coronary-vascular-dynamics of a control sample group against a pacing post-conditioning (PPC) group, a group treated with the method of preventing reperfusion injury in reperfusion therapy with a high dose (1.0 g/kg) of immunoglobulin treatment (IgH) pre-ischemia, and a group treated with the method of preventing reperfusion injury in reperfusion therapy with a low dose (0.6 g/kg) of immunoglobulin treatment (IgH) pre-ischemia.
Figure 2D:
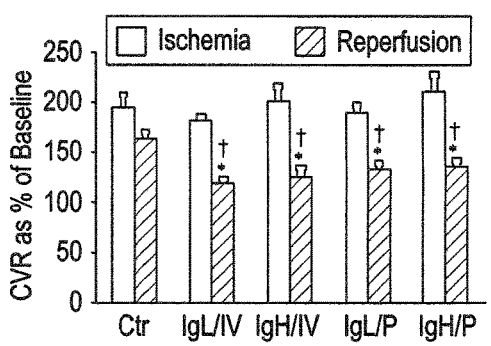
FIG. 2D is a graph comparing coronary vascular resistance (CVR) of the coronary-vascular-dynamics of a control sample group against a pacing post-conditioning (PPC) group, a group treated with the method of preventing reperfusion injury in reperfusion therapy with a high dose (1.0 g/kg) of immunoglobulin treatment (IgH) pre-ischemia, and a group treated with the method of preventing reperfusion injury in reperfusion therapy with a low dose (0.6 g/kg) of immunoglobulin treatment (IgH) pre-ischemia.
Figure 2E:
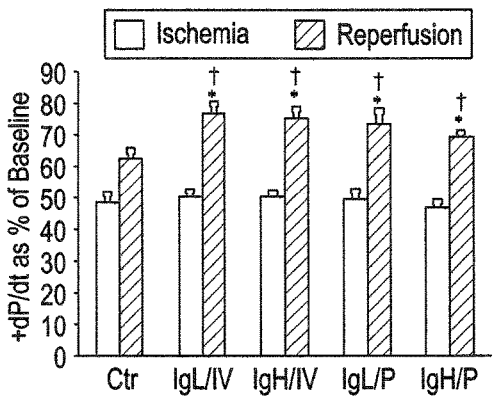
FIG. 2E is a graph comparing left ventricle (LV) contractility (+dP/dt) of a control sample group against a pacing post-conditioning (PPC) group, a group treated with the method of preventing reperfusion injury in reperfusion therapy with a high dose (1.0 g/kg) of immunoglobulin treatment (IgH) pre-ischemia, and a group treated with the method of preventing reperfusion injury in reperfusion therapy with a low dose (0.6 g/kg) of immunoglobulin treatment (IgH) pre-ischemia.
Figure 2F:
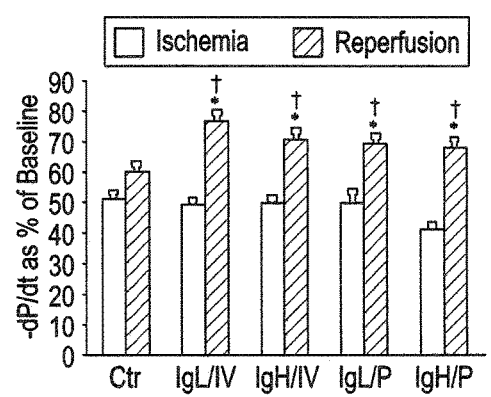
FIG. 2F is a graph comparing LV contractility (−dP/dt) of a control sample group against a pacing post-conditioning (PPC) group, a group treated with the method of preventing reperfusion injury in reperfusion therapy with a high dose (1.0 g/kg) of immunoglobulin treatment (IgH) pre-ischemia, and a group treated with the method of preventing reperfusion injury in reperfusion therapy with a low dose (0.6 g/kg) of immunoglobulin treatment (IgH) pre-ischemia.
Figure 3A:
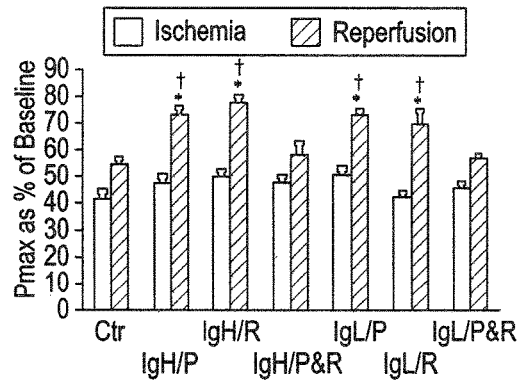
FIG. 3A is a graph comparing maximum developed pressure (Pmax) of the left ventricle function of a control sample group against a pacing post-conditioning (PPC) group, a group treated with the method of preventing reperfusion injury in reperfusion therapy with a high dose (1.0 g/kg) of immunoglobulin treatment (IgH) for combined pre-ischemia treatment and post-ischemia treatment, and a group treated with the method of preventing reperfusion injury in reperfusion therapy with a low dose (0.6 g/kg) of immunoglobulin treatment (IgH) for combined pre-ischemia treatment and post-ischemia treatment.
Figure 3B:
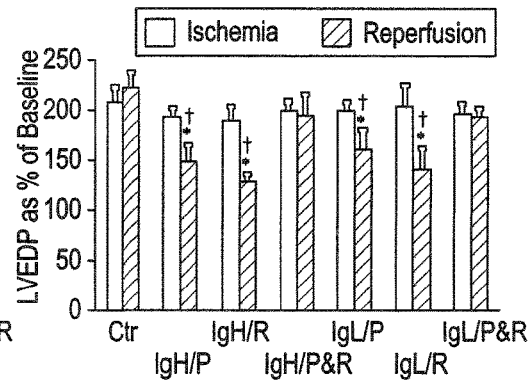
FIG. 3B is a graph comparing left ventricular end diastolic pressure (LVEDP) of the left ventricle function of a control sample group against a pacing post-conditioning (PPC) group, a group treated with the method of preventing reperfusion injury in reperfusion therapy with a high dose (1.0 g/kg) of immunoglobulin treatment (IgH) for combined pre-ischemia treatment and post-ischemia treatment, and a group treated with the method of preventing reperfusion injury in reperfusion therapy with a low dose (0.6 g/kg) of immunoglobulin treatment (IgH) for combined pre-ischemia treatment and post-ischemia treatment.
Figure 3C:
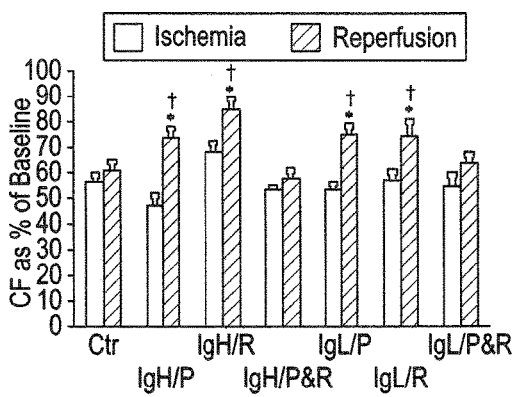
FIG. 3C is a graph comparing coronary flow (CF) of the coronary-vascular-dynamics of a control sample group against a pacing post-conditioning (PPC) group, a group treated with the method of preventing reperfusion injury in reperfusion therapy with a high dose (1.0 g/kg) of immunoglobulin treatment (IgH) for combined pre-ischemia treatment and post-ischemia treatment, and a group treated with the method of preventing reperfusion injury in reperfusion therapy with a low dose (0.6 g/kg) of immunoglobulin treatment (IgH) for combined pre-ischemia treatment and post-ischemia treatment.
Figure 3D:
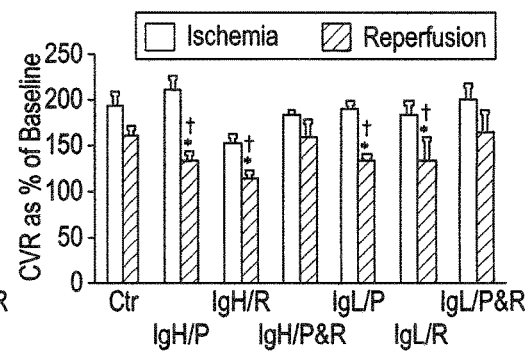
FIG. 3D is a graph comparing coronary vascular resistance (CVR) of the coronary-vascular-dynamics of a control sample group against a pacing post-conditioning (PPC) group, a group treated with the method of preventing reperfusion injury in reperfusion therapy with a high dose (1.0 g/kg) of immunoglobulin treatment (IgH) for combined pre-ischemia treatment and post-ischemia treatment, and a group treated with the method of preventing reperfusion injury in reperfusion therapy with a low dose (0.6 g/kg) of immunoglobulin treatment (IgH) for combined pre-ischemia treatment and post-ischemia treatment.
Figure 3E:
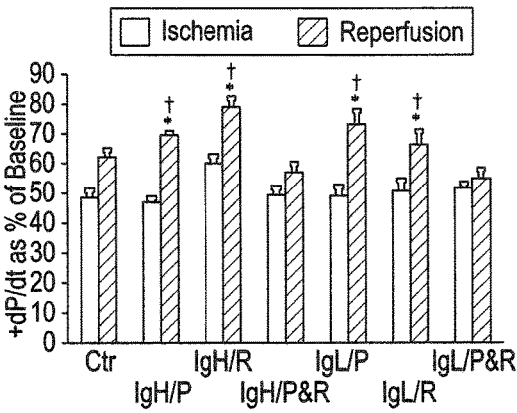
FIG. 3E is a graph comparing left ventricle (LV) contractility (+dP/dt) of a control sample group against a pacing post-conditioning (PPC) group, a group treated with the method of preventing reperfusion injury in reperfusion therapy with a high dose (1.0 g/kg) of immunoglobulin treatment (IgH) for combined pre-ischemia treatment and post-ischemia treatment, and a group treated with the method of preventing reperfusion injury in reperfusion therapy with a low dose (0.6 g/kg) of immunoglobulin treatment (IgH) for combined pre-ischemia treatment and post-ischemia treatment.
Figure 3F:
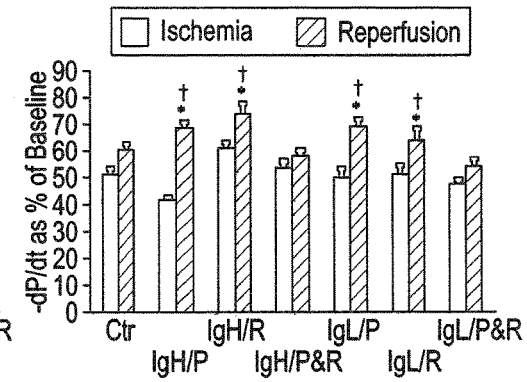
FIG. 3F is a graph comparing LV contractility (−dP/dt) of a control sample group against a pacing post-conditioning (PPC) group, a group treated with the method of preventing reperfusion injury in reperfusion therapy with a high dose (1.0 g/kg) of immunoglobulin treatment (IgH) for combined pre-ischemia treatment and post-ischemia treatment, and a group treated with the method of preventing reperfusion injury in reperfusion therapy with a low dose (0.6 g/kg) of immunoglobulin treatment (IgH) for combined pre-ischemia treatment and post-ischemia treatment.

The method of preventing reperfusion injury in reperfusion therapy can be used for prevention of reperfusion injury in a patient where reperfusion therapy is necessary, such as following an ischemic event. The ischemic event can include myocardial ischemia or heat transplant, for example. The patient is treated with intravenous immunoglobulin (IVIG) prior to the ischemic event (IVIG pre-treatment) or, alternatively, following the regional myocardial ischemia reperfusion (IVIG post-treatment), with the IVIG providing cardio-protective effects to the patient for preventing reperfusion injury. The treatment with the IVIG may be used with any suitable type of reperfusion therapy, such as thrombolytic therapy, coronary angioplasty, coronary artery bypass surgery or following heart transplantation, for example.

In either pre- or post-treatment of the patient with the IVIG, the patient is given from about 0.5 g to about 2.0 g of the IVIG per kilogram of patient body weight. This dosage may be a one-time dosage or may be delivered multiple times, dependent upon the particular situation. In order to investigate the effectiveness of immunoglobulins in the protection of the heart against ischemia reperfusion injury, male Wistar rats, weighing between 250 g and 300 g, were subjected to regional ischemia and reperfusion. The rats were anesthetized with intraperitoneal injection of sodium pentobarbital (60 mg/kg) and anticoagulated with heparin (1000 U/kg body weight) through the femoral vein and attached to a modified Langendorff setup for the perfused rat heart. The hearts were perfused retrogradely with freshly prepared Krebs-Hensleit solution. The buffer was gassed with a mixture of oxygen (95%) and $CO_2$ (5%), with a pH of 7.35-7.45 at a temperature of 37.0±0.5° C. The perfusion pressure (PP) was kept constant at 50 mm Hg throughout the experimental procedure in all of the protocols described herein. PP was measured immediately downstream from the flow probe in a branch of the aortic cannula using a Statham Physiological Pressure Transducer P23db, manufactured by Gould Inc. of Illinois.

Constant PP was ensured electronically by means of the perfusion assembly (Module PPCM, Type 671, manufactured by Hugo Sachs Elektronik of Germany). This system permits an accurate adjustment of PP between 5 and 150 mm Hg with an accuracy of ±1 mm Hg. The temperature of the perfusion medium in the perfusion system was maintained at 37° C. by circulating temperature controlled water. This temperature is the baseline control perfusion temperature for all protocols described below. Myocardial temperature was monitored by a needle thermistor probe (TH-5 Thermalert Monitoring Thermometer, manufactured by Physitemp® Instruments, Inc. of New Jersey) inserted at the apex of the heart for each protocol of the study.

The heart was instrumented with pacing electrodes on the right atrial (RA) appendage and posterior basal LV wall. The left descending coronary artery was encircled by a snare at approximately 0.5 cm below the atrioventricular groove and a deflated balloon catheter was positioned between the heart and the suture over the coronary artery. The aorta was cannulated, allowing retrograde perfusion of the heart with a preload of 6 mm Hg. Throughout the experiment, afterload was kept constant at 80 mm Hg.

The studies described below investigated the role of immunoglobulins pre- and post-treatments, or a combination thereof, on the heart protection against ischemia reperfusion I/R injury (FIG. 1). The pre-treatment protocol was subdivided into five groups: In the first group (group A), the control hearts (n=6) were subjected to I/R without any further treatment. In the second group (group B), the hearts (n=6) were subjected to FR and PPC; i.e., in group B, the hearts received the PPC protocol with three cycles of 30 seconds of left ventricle (LV) pacing alternated with 30 seconds of right atrial (RA) pacing. In the third group (group C), either low dose immunoglobulin (IgL) (0.6 g/kg) or high dose immunoglobulins (IgH) (1 g/kg) (n=6 each) were infused in the buffer during the stabilization period at 15 minutes before the index ischemia. In the fourth and fifth groups (group D) (n=6 each), the hearts were infused intravenously with either IgL or IgH two hrs before sacrifice and heart isolation.

For the post-treatment experiments, the hearts were isolated from untreated rats. The hearts in treatment group E were either treated with IgL or IgH (n=6 each) five minutes before reperfusion and the treatment was continued for ten minutes after the start of reperfusion. The hearts in a combined treatment group F were treated with either IgL or IgH in the buffer 15 minutes before ischemia and five minutes before reperfusion, and the treatment was continued for ten minutes thereafter (n=6).

In all hearts, the ischemia was produced by 30 minutes of coronary artery occlusion (CAO), followed by 30 minutes of reperfusion. In the pre-treatment groups, pre-treatment was performed after the stabilization period of the heart, followed by the index ischemia, followed by 30 minutes of reperfusion. In the post-treatment studies, the hearts were subjected to 30 minutes of CAO, followed by 30 minutes of reperfusion. All IVIG post-treatments were performed five minutes before the start of reperfusion, and PPC was performed at the beginning of reperfusion.

Coronary flow (CF) was measured continuously by an electromagnetic flow probe attached to the inflow of the aortic cannula. The probe was attached to a flow meter which was interfaced to a personal computer. The CF in ml/min was continuously monitored by timed collection of coronary effluent as well as computed. The coronary vascular resistance (CVR) was computed every ten seconds along with the hemodynamic data by an on-line data acquisition program (Isoheart software version 1.524-S, sold by Hugo-Sachs Electronik of Germany). Left ventricular Pmax and left ventricular end diastolic pressure (LVEDP) were measured by placing and securing a water-filled latex balloon into the left ventricular cavity. The balloon was attached to a pressure transducer and DC-bridge amplifier (DC-BA) of the pressure module (DC-BA type 660, manufactured by Hugo-Sachs Electronik of Germany) and interfaced to a personal computer for on-line monitoring of left ventricular pressure and its derivatives. Left ventricular Pmax was derived from the online acquisition of left ventricular systolic pressure (LVSP) by a Max-Min module. This module converts the output from the DC-BA to Pmax by subtracting LVEDP from the maximal LVSP.

Infarct size was determined by triphenyltetrazolium chlorile (TTC). The hearts were collected after 30 minutes of reperfusion and stored overnight at −20° C. The next day, the hearts were cut into 4-5 pieces from apex to base, incubated in TTC (1%) solution in isotonic pH 7.4 phosphate buffer and fixed with formaldehyde (4%). Images were taken using a camera. Red and pale unstained areas of every slice were indicated manually on the image and corresponding areas were quantified using ImageJ, a software package provided by the United States National Institutes of Health. The ratio of infarct size to LV area was calculated and expressed as a percentage for each heart.

For an assessment of apoptosis, a terminal deoxnucleotidyl transferase mediated UTP nick end labeling (TUNEL) assay was used. Three micrometer thick paraffin sections were de-waxed by submerging in xylene, rehydrated by passing through descending grades of alcohol (100%-70% alcohol), washed with distilled water and phosphate buffer saline (PBS), immersed in antigen retrieval solution (sodium citrate buffer formed as a mixture of 13.5 ml of 21 g of citric acid monohydrate in 1 liter of distilled water and 61.5 ml of 29.4 g of sodium citrate dehydrate in 1 liter of distilled water, made up to 750 ml with distilled water) for five minutes in a microwave oven at medium power. Tissue sections were brought to room temperature, kept in PBS for five minutes, in Triton X-100 solution (0.1% in PBS) for eight minutes and washed twice with PBS. 50 µl of TUNEL reaction mixture (50 µl of enzyme solution formed from terminal deoxynucleotidyl transferase from calf thymus in storage buffer, and 450 µl of labeling solution formed from nucleotide in reaction buffer) was added onto the section until the whole tissue was covered.

The negative control section was covered only with 50 µl of labeling solution. The slides were incubated in a humidified chamber for one hour at 37° C., rinsed three times in PBS and freshly prepared 4' 6-diamindino-2-phenylindole (DAPI) (1:4000) was added onto the tissue section for one minute and the sections were mounted in Vectashield®, manufactured by Vector Laboratories, Inc. of California. The edges of the cover slips were sealed by nail polish. The slides were examined in a confocal microscope and selected areas were photographed. Ten fields/hearts were examined and TUNEL positive myocytes nuclei were counted such that the mean values were obtained. A Roche® In situ Cell Death Detection Kit, Fluorescein was used for this purpose.

All samples were immediately frozen in liquid nitrogen and subsequently stored at −80° C. All of the data collected are presented as mean±SE. One-way analysis of variance (ANOVA) for repeated measures within each group and between the groups was performed on absolute values, even when presented as % of baseline. Only if this analysis showed a significant difference, post hoc analysis was used for further comparison. P<0.05 is considered statistically significant for the below data.

FIGS. 1A-1F are graphs comparing results for post-ischemia treatment for a control sample group (Ctr) with a pacing post-conditioning (PPC) group, a group treated with a high dose (1.0 g/kg) of immunoglobulin treatment (IgH), and with a group treated with a low dose (0.6 g/kg) of immunoglobulin treatment (IgH). Results are shown for left ventricle function (Pmax) in FIG. 1A, left ventricle function (LVEDP) in FIG. 1B, coronary-vascular-dynamics (CF) in FIG. 1C, coronary-vascular-dynamics (CVR) in FIG. 1D, LV contractility (+dP/dt) in FIG. 1E, and LV contractility (−dP/dt) in FIG. 1F post-ischemic recovery after PPC and IVIG treatment protocols. The data was computed at 30 minutes following reperfusion and expressed as mean±SEM. Similar to pacing post-conditioning (PPC), both low and high immunoglobulin treatment protocols given post-ischemia showed cardio-protective effects. Here, PPC and immunoglobulin infusion at reperfusion (both IgL and IgH) showed cardio-protective effects by means of LV function, coronary-vascular-dynamics and LV contractility. For this data, P<0.05 compared to respective controls and P<0.01 compared to ischemic period for PPC. P<0.01 compared to ischemic period for IVIG treatments. There are no statistical differences when PPC, IgL and IgH were compared with each other. In FIGS. 1A-1F, "R" represents reperfusion.

Similarly, FIGS. 2A-2F compare results is a graph comparing results for pre-ischemia treatment for a control sample group (Ctr) against a pacing post-conditioning (PPC) group, a group treated with a high dose (1.0 g/kg) of immunoglobulin treatment (IgH), and a group treated with a low dose (0.6 g/kg) of immunoglobulin treatment (IgH). Results are shown for left ventricle function (Pmax) in FIG. 2A, left ventricle function (LVEDP) in FIG. 2B, coronary-vascular-dynamics (CF) in FIG. 2C, coronary-vascular-dynamics (CVR) in FIG. 2D, LV contractility (+dP/dt) in FIG. 2E, and LV contractility (−dP/dt) in FIG. 2F. The data was collected for IVIG pre-treatment infusion either in the buffer during the stabilization period 15 minutes before the index ischemia, or infusion intravenously within two hours before sacrificing the rats and heart isolation. The data clearly show cardio-protective effects by means of LV function, coronary-vascular-dynamics and LV contractility. Here, P<0.01 compared to the ischemic period for PPC. Additionally, P<0.001 compared to ischemic period. There are no statistical differences when IgL and IgH were compared with each other. In FIGS. 2A-2F, "IV" represents intravenous, and "P" represents pretreatment.

FIGS. 3A-3F show similar data, but for combined pre-ischemia treatment and post-ischemia treatment with the IVIG. Combined immunoglobulin (both IgL and IgH) pre- and post-treatment infusion showed no cardio-protective effects by means of LV function, coronary-vascular-dynamics and LV contractility. This is in contrast to either pre- or post-treatment given alone. The pretreatment protocol was performed using IVIG infusion in the buffer. Here, P<0.01 compared to respective controls, and P<0.01 compared to ischemic period for IVIG at reperfusion (IgH/R and IgL/R). There are no statistical differences when IgL and IgH were compared with each other.

Figure 4A:
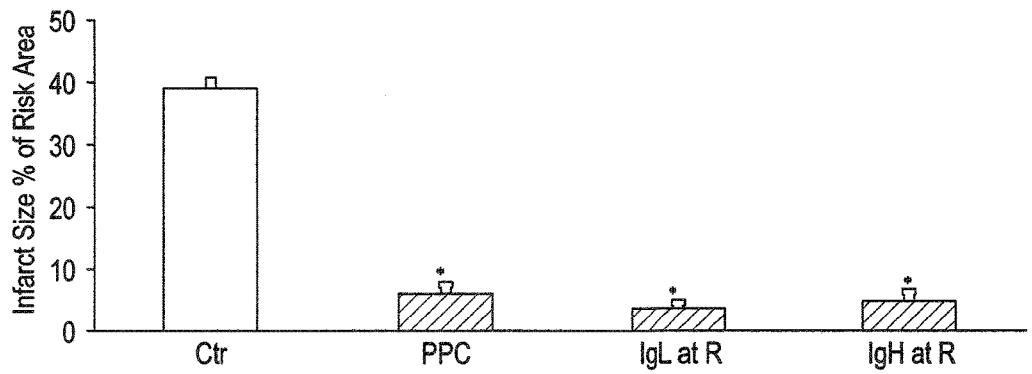
FIG. 4A is a graph comparing infarct size of a control sample group against a pacing post-conditioning (PPC) group, a group treated with the method of preventing reperfusion injury in reperfusion therapy with a high dose (1.0 g/kg) of immunoglobulin treatment (IgH) for post-ischemia treatment, and a group treated with the method of preventing reperfusion injury in reperfusion therapy with a low dose (0.6 g/kg) of immunoglobulin treatment (IgH) for post-ischemia treatment.
Figure 4B:
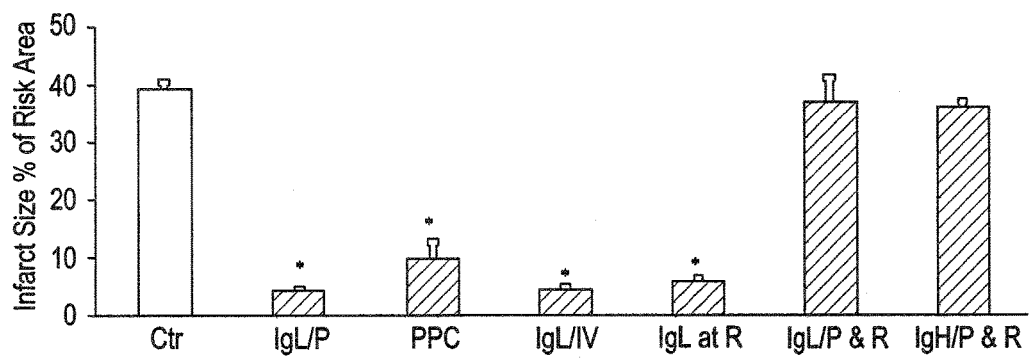
FIG. 4B is a graph comparing infarct size of a control sample group against a pacing post-conditioning (PPC) group, a group treated with the method of preventing reperfusion injury in reperfusion therapy with a high dose (1.0 g/kg) of immunoglobulin treatment (IgH) for post-ischemia treatment, a group treated with the method of preventing reperfusion injury in reperfusion therapy with a low dose (0.6 g/kg) of immunoglobulin treatment (IgH) for post-ischemia treatment, a group treated with the method of preventing reperfusion injury in reperfusion therapy with a high dose (1.0 g/kg) of immunoglobulin treatment (IgH) for combined pre-ischemia and post-ischemia treatment, and a group treated with the method of preventing reperfusion injury in reperfusion therapy with a low dose (0.6 g/kg) of immunoglobulin treatment (IgH) for combined pre-ischemia and post-ischemia treatment.

Additionally, immunoglobulin infusion at reperfusion, both at the low (0.6 g/kg) and high doses (1 g/kg), showed significant reduction in infarct size compared to the control group but comparable to the PPC group (see FIG. 4A). Similar effects were found when IVIG (IgL at 0.6 g/kg or IgH at 1 g/kg) was given during the pre-treatment protocol either in the buffer 15 minutes before the index ischemia or infusion intravenously within two hours before sacrificing the rats and heart isolation (FIG. 4B). However, combined pre- and post-treatment with IVIG showed no differences in the infarct size compared to the control group (FIG. 4B). One can see in FIG. 4A that PPC and IVIG at reperfusion decreased infarct size. As can be seen in FIG. 4B, IVIG pre-treatment decreased infarct size while combined pre- and post-treatment with IVIG showed no differences in the infarct size compared to the control group. Here, P<0.001 compared to respective controls.

Figure 5:
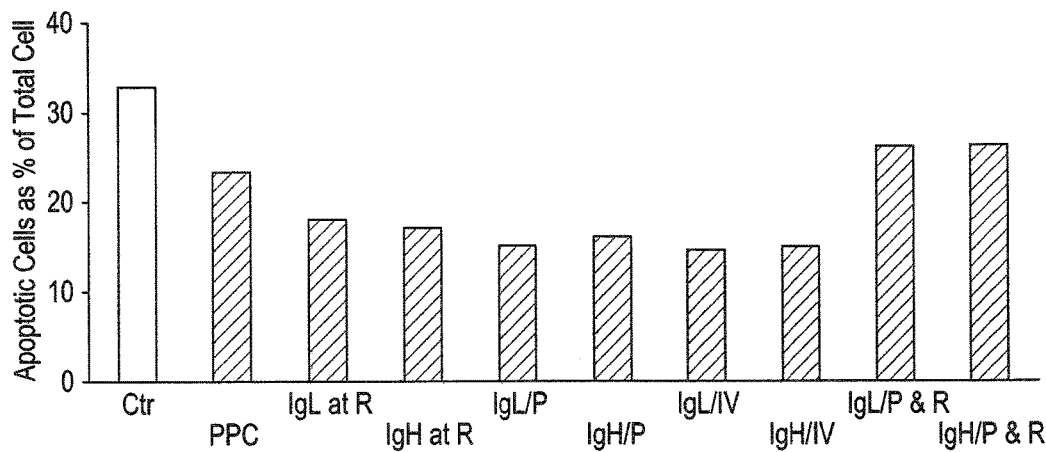
FIG. 5 is a graph comparing mytocyte apoptosis of a control sample group against a pacing post-conditioning (PPC) group, a group treated with the method of preventing reperfusion injury in reperfusion therapy with a high dose (1.0 g/kg) of immunoglobulin treatment (IgH) for post-ischemia treatment, a group treated with the method of preventing reperfusion injury in reperfusion therapy with a low dose (0.6 g/kg) of immunoglobulin treatment (IgH) for post-ischemia treatment, a group treated with the method of preventing reperfusion injury in reperfusion therapy with a high dose (1.0 g/kg) of immunoglobulin treatment (IgH) for combined pre-ischemia and post-ischemia treatment, and a group treated with the method of preventing reperfusion injury in reperfusion therapy with a low dose (0.6 g/kg) of immunoglobulin treatment (IgH) for combined pre-ischemia and post-ischemia treatment.

With regard to apoptosis, IVIG administration given as infusion at reperfusion or pre-treatment, either in the buffer during the stabilization period 15 minutes before the index ischemia or infusion intravenously within two hours before sacrificing the rats and heart isolation, either in low doses (0.6 g/kg) or high doses (1 g/kg), resulted in a marked decrease in myocytes apoptosis. This effect was less prominent when IVIG was given as combined pre- and post-treatment. FIG. 5 illustrates the IVIG effects on myocytes apoptosis. As shown, IVIG resulted in a decrease of myocytes apoptosis.

It is to be understood that the present invention is not limited to the embodiments described above, but encompasses any and all embodiments within the scope of the following claims.

We claim:

1. A method of alleviating reperfusion injury in reperfusion therapy, comprising the steps of:
    performing regional myocardial ischemia reperfusion on a patient; and
    treating the patient with an effective amount of intravenous immunoglobulin after an ischemic event, wherein the intravenous immunoglobulin has a cardio-protective effect to alleviate reperfusion injury in the patient, wherein the effective amount of the intravenous immunoglobulin comprises treating the patient with from 0.6 g to 1.0 g of the intravenous immunoglobulin per kilogram of body weight of the patient.

2. The method of preventing reperfusion injury in reperfusion therapy as recited in claim 1, wherein the step of performing regional myocardial ischemia reperfusion on the patient comprises performing thrombolytic therapy on the patient.

3. The method of preventing reperfusion injury in reperfusion therapy as recited in claim 1, wherein the step of performing regional myocardial ischemia reperfusion on the patient comprises performing coronary angioplasty on the patient.

4. The method of preventing reperfusion injury in reperfusion therapy as recited in claim 1, wherein the step of performing regional myocardial ischemia reperfusion on the patient comprises performing coronary artery bypass surgery on the patient.

5. The method of preventing reperfusion injury in reperfusion therapy as recited in claim 1, wherein the step of performing regional myocardial ischemia reperfusion on the patient comprises performing post-heart transplantation reperfusion on the patient.

* * * * *